US009044211B2

(12) United States Patent
Ginn et al.

(10) Patent No.: US 9,044,211 B2
(45) Date of Patent: *Jun. 2, 2015

(54) LOCATOR AND CLOSURE DEVICE AND METHOD OF USE

(75) Inventors: Richard S. Ginn, Gilroy, CA (US);
Thomas J. Palermo, San Jose, CA (US)

(73) Assignee: CORDIS CORPORATION

( * ) Notice: Subject to any disclaimer, the term of this patent is extended or adjusted under 35 U.S.C. 154(b) by 0 days.

This patent is subject to a terminal disclaimer.

(21) Appl. No.: 13/331,292

(22) Filed: Dec. 20, 2011

(65) Prior Publication Data

US 2012/0089179 A1    Apr. 12, 2012

Related U.S. Application Data

(63) Continuation of application No. 11/244,944, filed on Oct. 5, 2005, now Pat. No. 8,088,144.

(60) Provisional application No. 60/677,859, filed on May 4, 2005.

(51) Int. Cl.
*A61B 17/08* (2006.01)
*A61B 17/00* (2006.01)
*A61B 17/29* (2006.01)
*A61B 19/00* (2006.01)

(52) U.S. Cl.
CPC ... *A61B 17/0057* (2013.01); *A61B 2017/00654* (2013.01); *A61B 2017/00672* (2013.01); *A61B 2017/2923* (2013.01); *A61B 2019/4836* (2013.01)

(58) Field of Classification Search
CPC .............. A61B 17/0057; A61B 2017/00654; A61B 2017/2923; A61B 2019/4836; A61B 2017/00672; A61B 2017/00637
See application file for complete search history.

(56) References Cited

U.S. PATENT DOCUMENTS

| 4,586,502 | A  | * | 5/1986  | Bedi et al. ..................... 606/144 |
| 5,224,949 | A  | * | 7/1993  | Gomringer et al. ........... 606/159 |
| 5,324,306 | A  | * | 6/1994  | Makower et al. ............. 606/213 |
| 5,431,639 | A  | * | 7/1995  | Shaw ............................ 604/264 |
| 5,810,810 | A  | * | 9/1998  | Tay et al. ........................ 606/50 |
| 6,818,008 | B1 | * | 11/2004 | Cates et al. ................... 606/213 |
| 2002/0077658 | A1 | * | 6/2002 | Ginn ............................. 606/213 |

* cited by examiner

*Primary Examiner* — Elizabeth Houston
*Assistant Examiner* — Son Dang

(57) ABSTRACT

The present invention is directed to a device which is capable of both locating a punctured blood vessel wall and sealing the puncture in the vessel and to the method of using the device as well. In one embodiment, the device includes an elongate deployment member having a sealing element releasably disposed within a distal end thereof, said deployment member being coupled to a first actuator configured to retract said deployment member relative to said sealing element, and an elongated indicator member having a proximal end and a distal end, said indicator member extending through a lumen in said deployment member such that the distal end of said indicator member extends distally of the distal end of the deployment member, and said indicator member being coupled to a second actuator configured to retract said indicator member relative to said deployment member.

12 Claims, 6 Drawing Sheets

LOCATOR AND CLOSURE DEVICE AND METHOD OF USE

RELATED APPLICATION

This application is a continuation of U.S. application Ser. No. 11/244,944, filed Oct. 5, 2005, which claims the benefit of U.S. Provisional Application Ser. No. 60/677,859, filed May 4, 2005, and is related to U.S. application Ser. No. 10/687,848 filed Oct. 17, 2003 and Ser. No. 10/850,795 filed May 21, 2004, the disclosures of which are incorporated in their entirety herein.

FIELD OF THE INVENTION

The present invention relates generally to apparatus and methods for sealing or closing passages through tissue, and more particularly to devices for sealing punctures or other openings communicating with body lumens, such as blood vessels, and to apparatus and methods for delivering such devices.

BACKGROUND OF THE INVENTION

Catheterization and interventional procedures, such as angioplasty and stenting, generally are performed by inserting a hollow needle through a patient's skin and muscle tissue into the vascular system. This creates a puncture wound in a blood vessel, frequently the femoral artery, which, once the interventional procedure has been completed, needs to be closed or sealed in a suitable manner. Procedures and devices have been proposed for accomplishing such closure which involve the use of an introducer sheath that is placed in the tract of the puncture wound following which a closure delivering device is introduced through the introducer sheath to deploy a sealing element within the tract. An indicator wire may be used to locate the edge of the tract. After the closure delivering device deploys the sealing element, the indicator wire and the device are retracted. Examples of such procedures and devices are disclosed in application Ser. No. 10/687,848, filed Oct. 17, 2003 and Ser. No. 10/850,795 filed May 21, 2004. In these procedures and devices, it would be desirable to have a mechanism that prevents a user from prematurely retracting the closure delivering device when deploying the sealing element. Further, it would be desirable to have a mechanism that prevents the indicator wire from interfering with the deployment of the sealing element.

SUMMARY OF THE INVENTION

The present invention is directed to a device which is capable of both locating a punctured blood vessel wall and sealing the puncture in the vessel and to the method of using the device as well.

In one embodiment, the device includes an elongate deployment member having a sealing element releasably disposed within a distal end thereof, said deployment member being coupled to a first actuator configured to retract said deployment member relative to said sealing element, and an elongated indicator member having a proximal end and a distal end, said indicator member extending through a lumen in said deployment member such that the distal end of said indicator member extends distally of the distal end of the deployment member, and said indicator member being coupled to a second actuator configured to retract said indicator member relative to said deployment member.

In another embodiment, the device includes an indicator that notifies the operator when the distal end of the indicator member is positioned at a desirable location within the puncture.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

DESCRIPTION OF THE DRAWINGS

In order to better appreciate how the above-recited and other advantages and objects of the present inventions are obtained, a more particular description of the invention briefly described above will be rendered by reference to specific embodiments thereof, which are illustrated in the accompanying drawings. It should be noted that the components in the figures are not necessarily to scale, emphasis instead being placed upon illustrating the principles of the invention. Moreover, in the figures, like reference numerals designate corresponding parts throughout the different views. However, like parts do not always have like reference numerals. Moreover, all illustrations are intended to convey concepts, where relative sizes, shapes and other detailed attributes may be illustrated schematically rather than literally or precisely.

DETAILED DESCRIPTION OF THE INVENTION

Figure 1:
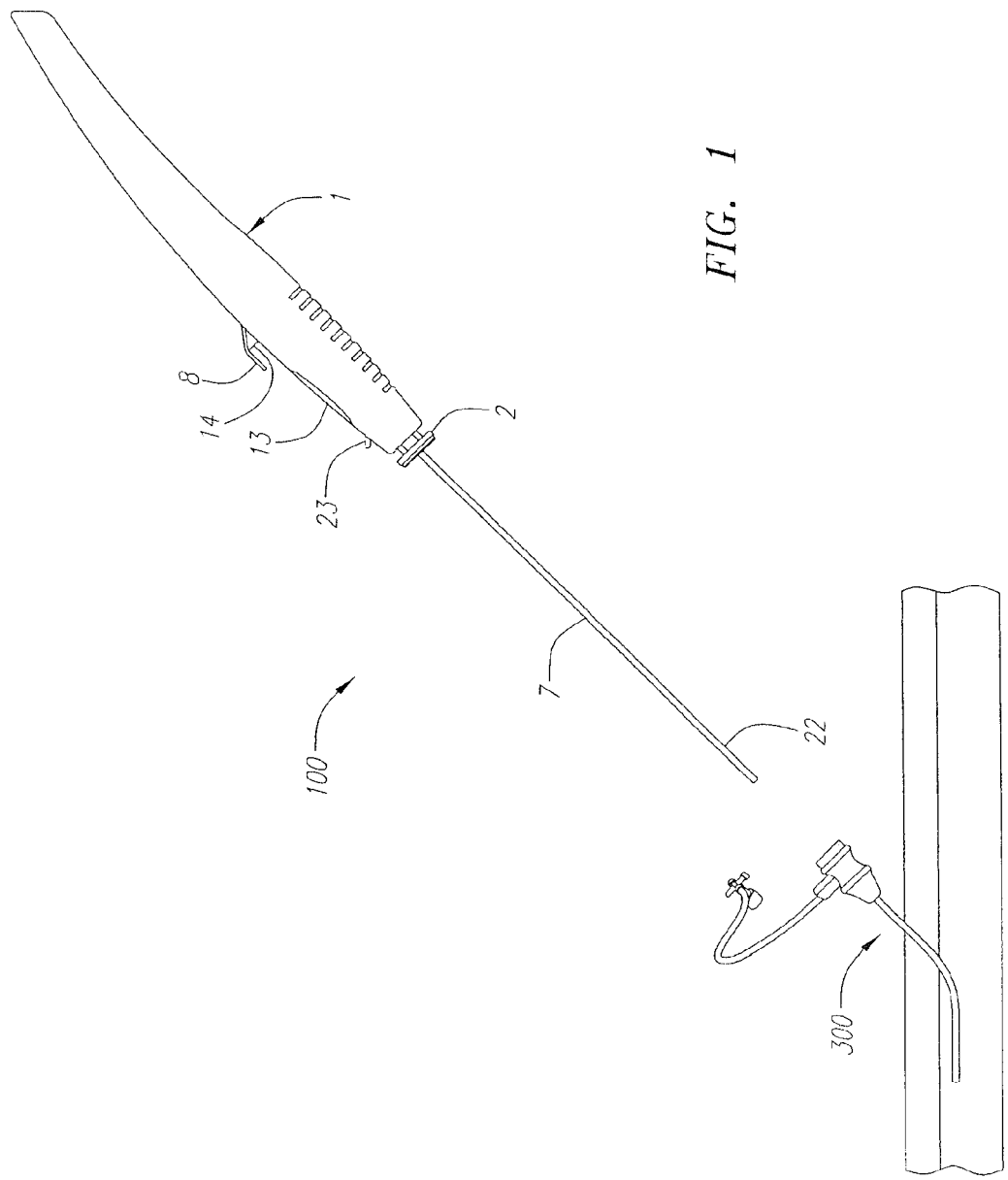
FIG. 1 illustrates a side-view of a sealing element deployment device in accordance with a preferred embodiment of the present invention.

A device 100 for deploying a detachable sealing element 160 (shown in FIG. 2) in a puncture wound is shown in FIG. 1, herein referred to as a closure device 100. Examples of such a sealing element or plug 160 are described in U.S. application Ser. No. 10/687,848, filed Oct. 17, 2003, Ser. No. 10/850, 795 filed May 21, 2004, and Ser. No. 11/038,995, filed Jan. 19, 2005, each of which applications are hereby incorporated by reference. Sealing element 160 occludes blood flow from a puncture. In a preferred embodiment, the sealing element 160 will be fabricated from a material which expands upon contact with blood such as a felt made from polyglycolic acid and/or polylactic acid polymers or copolymers or other materials such as collagens. The sealing element 160 may also have one or more hemostasis, antibiotic or other therapeutic agents added to it.

Alternatively, in other preferred embodiments, the sealing element 160 will be made in such a manner that it will expand spontaneously or upon removal of a restraining force. In still other embodiments, the sealing element 160 can be expandable mechanically, hydraulically or pneumatically. In all such embodiments, it is preferred that the sealing element 160 be fabricated from a bioabsorbable material.

The closure device 100 for deploying the sealing element 160 includes a tubular elongate member 1, herein referred to as the "housing," which houses various components that will be described below. The device 100 also comprises a wire actuator 2 which is external and distal to the housing 1 and is slidably mounted and configured to actuate an indicator wire 6, as described below. Extending through the distal end of the housing 1 is a deployment tube 7 configured to be received by an introducer sheath 300 known in the art. The deployment tube 7 is slightly longer than the introducer sheath 300. The deployment tube 7 receives an indicator wire 6 (shown in FIGS. 2a and 2b) and a pusher 80, which operates as a backing member supporting a detachable sealing element 160 at a distal section of the deployment tube 7. The pusher 80 preferably includes a channel through which the indicator wire 6 may be received within the tube 7. The channel is preferably located on or near the edge or the periphery of the backing portion of the pusher 80, i.e., near the internal surface of the deployment tube 7. Optionally, an indicator wire tube or other lumen (not shown) may be provided within the interior of the deployment tube 7. The indicator wire tube is preferably attached to the housing 1 at its proximal end, and extends through the deployment tube 7. The indicator wire 6 then extends through the indicator wire tube or other lumen and exits the indicator wire tube at or near the distal end of the deployment tube 7. (Additional details of the structure and operation of the pusher 80 are described in Ser. No. 10/850, 795, filed May 21, 2004, which is incorporated by reference)

The deployment tube 7 includes an inlet port 22 in the distal section of the tube 7, configured to take in blood when exposed to a vessel, and the housing 1 includes an outlet port 23 communicatively coupled to the inlet port 22 for allowing the blood to exit outside of the puncture wound. Also extending out of the housing is a trigger 8 that preferably includes a rotary link 14 configured to deploy the detachable sealing element 160. Before operation of the closure device 100, the rotary link 14 is locked, i.e., the operator is prevented from actuating the rotary link 14 despite pressing the trigger 8, as described below.

Turning to FIGS. 2(A-D), deployment of a detachable sealing element 160 within a puncture wound 400 using the closure device 100 is illustrated. An introducer sheath 300 is already deployed within the tract 410 of the wound 400 with its distal end 310 exposed within the lumen 420 of a blood vessel defined by a vessel wall 430. The deployment tube 7 of the closure device 100 is inserted into the introducer sheath 300. Upon substantially complete insertion, the device 100 is engaged with the introducer sheath 300, and the distal section of the deployment tube 7 extends out of the distal end of the sheath 300. When the inlet port 22 is exposed to the lumen 420 of the vessel 430, blood will enter the inlet port 22 and travel out of the outlet port 23 extending out of the housing 1. The blood exiting the outlet port 23 will be visible to the operator (not shown) of the device 100, notifying the operator that the distal end of the deployment tube 7 is within the lumen 420 of the vessel 430 and outside of the tract 410 of the puncture wound 400.

Also upon substantially complete insertion, the wire actuator 2 of the device 100 is actuated by the proximal end of the sheath 300, causing the wire actuator 2 to be pushed toward the housing 1. The wire actuator 2 is mechanically coupled to the indicator wire 6 and configured to actuate the indicator wire 6 in the distal direction. Thus, as the wire actuator 2 is pushed towards the housing 1, the wire actuator 2 causes the indicator wire 6 to extend out of the distal end of the deployment tube 7. When the indicator wire 6 exits the tube 7, the distal section of the wire 6 forms into a loop 5 located adjacent the distal tip of the tube 7. The loop 5 of the wire 6 will come into contact with the vessel wall 430 near the edge 415 of the tract 410 when the device 100 and the sheath 300 are withdrawn, as shown in FIG. 2b.

Figure 2A:
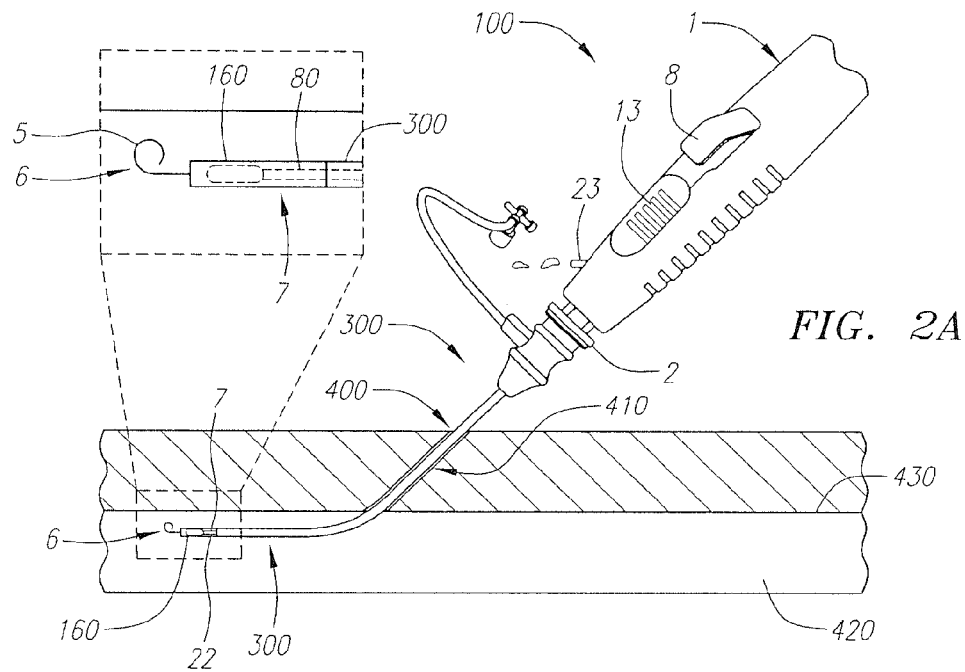
FIG. 2A illustrates a side-view of a sealing element deployment device in accordance with a preferred embodiment of the present invention.
Figure 2B:
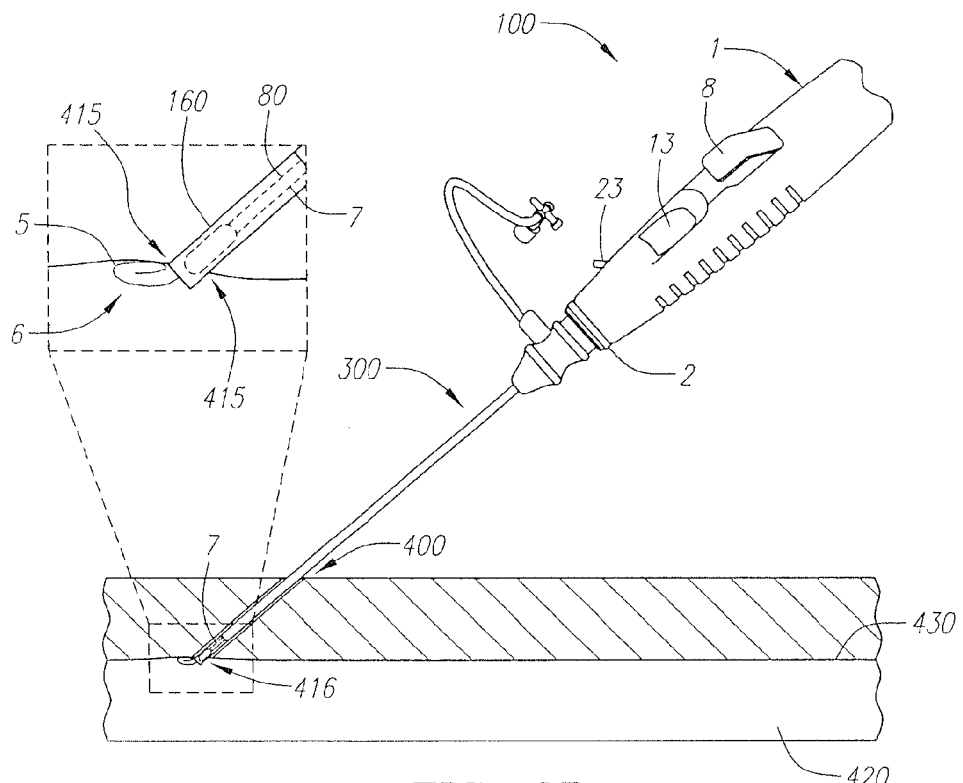
FIG. 2B illustrates a side-view of a sealing element deployment device in accordance with a preferred embodiment of the present invention.

Turning to FIG. 2b, after the device 100 is inserted and engaged into the sheath 300 as described above, the operator withdraws or pulls back the device 100 and sheath 300 within the tract 410. When the distal section of the deployment tube 7 exits the lumen 420 and enters the tract 410, the inlet port 22 is no longer exposed to the blood within the lumen 420 and thus, the blood flow out of the outlet port 23 ceases. This notifies the operator that the distal section of the deployment tube 7 has exited the lumen 420 and entered the tract 410 of the puncture wound 400. The indicator wire's 6 resistance that is caused by the loop 5 engaging the vessel wall 430 will unlock the rotary link 14, as described below, and optionally toggle the indicator window 13 to a state that indicates that the loop 5 has engaged the vessel wall 430 near the edge 415 of the tract 410, which places the distal end of the deployment tube 7 at a desirable location within the tract 410 and substantially adjacent to the edge 415. In the embodiment shown in FIG. 2b, the indicator window 13 toggles from a striped pattern, FIG. 2a, to a solid pattern, as described below.

Figure 2C:
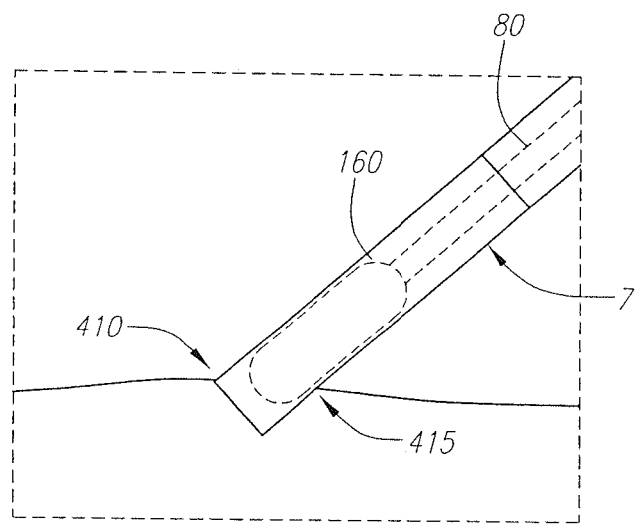
FIG. 2C illustrates a side-view of a distal portion of the sealing element deployment device in accordance with a preferred embodiment of the present invention.
Figure 2D:
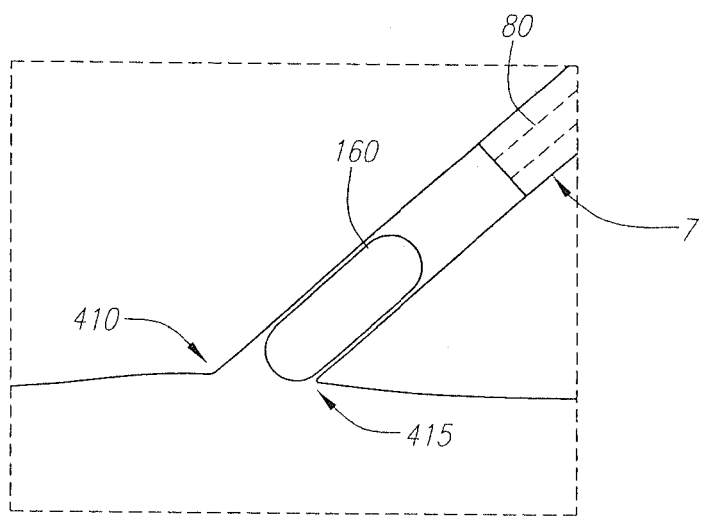
FIG. 2D illustrates a side-view of a distal portion of the sealing element deployment device in accordance with a preferred embodiment of the present invention.

The operator is then enabled to actuate the unlocked rotary link 14 to deploy the sealing element 160 by pressing the trigger 8. Turning to FIGS. 2C and 2D, the rotary link 14 actuates and withdraws both the wire 6 and the tube 7 while the sealing element 160 remains substantially in place by the pusher 80, thereby deploying the sealing element 160. The device 100 then disengages from the sealing element 160, thus sealing or plugging the puncture wound 400. Preferably, in one motion, the rotary link 14 is configured to withdraw the indicator wire 6 into the tube 7 before the tube 7 is withdrawn. Thus, the wire 6 is withdrawn before the sealing element 160 deployed, preventing the wire 6 from interfering with the deployment of the sealing element 160, such as damaging or dislodging the sealing element 160.

Figure 3:
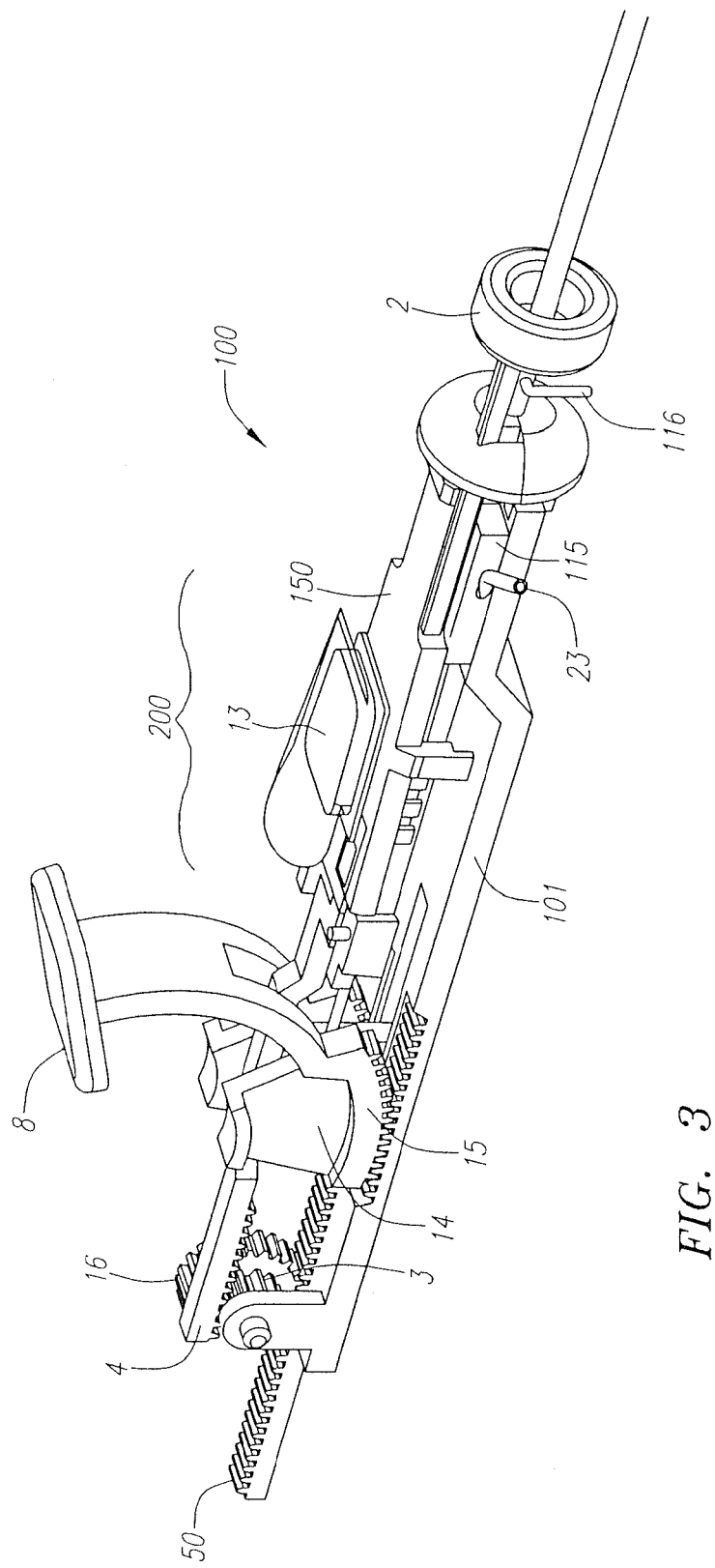
FIG. 3 illustrates a perspective view of components of a sealing element deployment device in accordance with a preferred embodiment of the present invention.

Turning to FIG. 3, a rack and pinion system for actuating the tube 7 and the wire 6 within the housing 1 of the device 100 is shown. The device 100 is shown not engaged to a introducer sheath 300, and thus the wire actuator 2 is in its original state away from the housing 1. The wire actuator 2 is coupled to a first rack 4 that is configured to engage a first gear 3 when the wire actuator 2 is actuated in the proximal direction as described above. The first gear 3 is attached to a second gear 16, which causes a second rack 50 to move in the distal direction. The second rack 50 is engaged with the indicator wire 6, causing the indicator wire 6 to extend out of the tube 7 when wire actuator 2 is actuated by engaging with the introducer sheath 300 as described above. The wire actuator 2 proximally withdraws the first rack 4, which rotates the second gear 16 via the first gear 3, which then advances distally the second rack 50, thus advancing distally the indicator wire 6, causing the indicator wire to extend out of the deployment tube 7.

The first and second gears 3 and 16 share an axis that is secured by a bottom plate 101. The bottom plate 101 is actuated by a trigger that includes a rotary link 14. When the trigger 8 is pressed to deploy the plug 160, the rotary link 14, which includes an arcuate gear section 15 that engages and actuates the bottom plate 101 in the proximal direction, is actuated. A tube collar 115, which is engaged to the deployment tube 7, is anchored at a distal portion of the bottom plate 101. When the bottom plate 101 is withdrawn proximally, the collar tube 115 is withdrawn as well, which in turn withdraws proximally the deployment tube 7, which deploys the plug 160. Proximally withdrawing the bottom plate 101 causes the first gear 3 to rotate along the first rack 4, which is locked in place by the wire actuator 2 engaged with the introducer sheath 300. Proximal to the wire actuator 2 is a post 116 that extends from the housing 1. When the distal portion of the closure device 100 is inserted into the lumen of the introducer sheath 300, a proximal portion of the introducer sheath 300 that defines a lip (not shown) engages the post 116, which connects and locks the closure device 100 to the introducer sheath 300. Thus, the second rack 50 is proximally withdrawn by the second gear 16, which causes the indicator wire 6 to retract substantially simultaneously with the deployment tube 7. The figures show that the first gear 3 has a smaller diameter than the second gear 16. First and second gears 3 and 16 each provide a mechanical advantage to the control of the indicator wire 6 and deployment tube 7 respectively. Preferably, the mechanical advantage regarding the indicator wire 6 is 4:1 and the mechanical advantage regarding the deployment tube 7 is 2:1. Other mechanical advantage relationships may be used e.g., 3:1 for the indicator wire 6 and 1.5:1 for the tube 7. It is preferred that the mechanical advantage for the indicator wire 6 be twice that for the tube 7. Thus, when trigger 8 is depressed, the bottom plate 101 and tube collar 115 will withdraw the tube 7 more slowly than the indicator wire 6 is withdrawn into the device 100 and the indicator wire 6 will be retracted into the deployment tube 7 before the sealing element 160 is deployed and/or disengaged from the tube 7 and the device 100. As described above, this advantageously prevents the indicator wire 6 from interfering with the deployment of the sealing element 160.

One of ordinary skill in the art will appreciate that though a rack and pinion system is described and shown in FIG. 3, any suitable type of actuating system may be configured to retract the indicator wire 6 before a sealing element 160 is deployed and/or disengaged from the device 100 in accordance with a preferred embodiment of the present invention. For example, a hydraulic, electronic, and/or a pulley system may be used instead of or in addition to the rack and pinion system to retract the indicator wire 6 into the deployment tube 7 before the sealing element 160 is deployed and/or disengaged from the device 100.

Figure 4A:
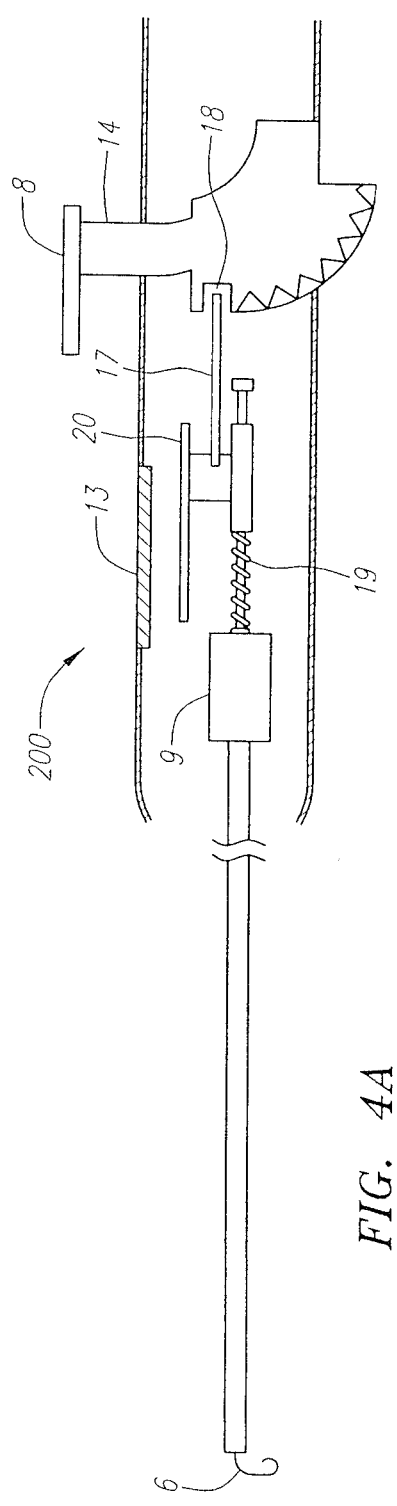
FIGS. 4(a-b) illustrate a distal portion of the device in accordance with a preferred embodiment of the present invention.
Figure 4B:
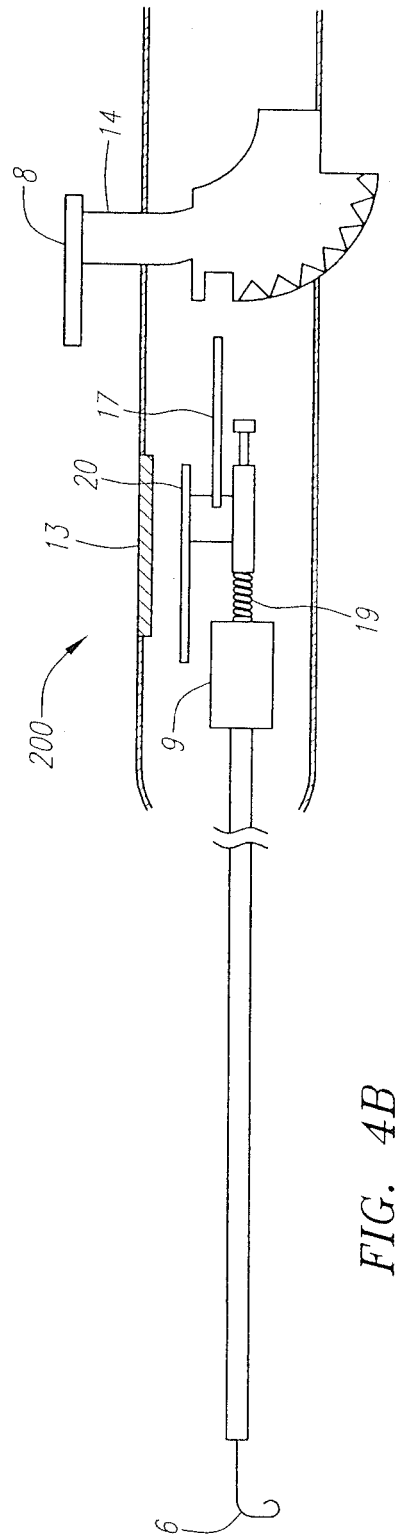

The housing 1 can also include an indicator assembly 200 coupled to a stationary top plate 150 of the device 100. The indicator assembly 200 can indicate to the operator, via an indicator panel 13 in the top plate 150, whether the distal end of the deployment tube 7 is in the desired location, e.g., near the edge 415 of the tract 410 of the puncture wound. In addition to, or in the alternative, the indicator assembly 200 may further lock the trigger 8 until the deployment tube 7 is in the desired location. In FIGS. 4A and 4B, an implementation of the indicator assembly 200 of the device 100 is shown. The indicator assembly 200 comprises an indicator 20, indicator spring 19 and lockout plate 17. As can be seen from FIG. 4A, a slidable lockout plate 17 engages groove 18 in rotary link 14, thereby preventing substantial movement of rotary link 14. The indicator spring 19 applies a proximal force on the lockout plate 17 to maintain the lockout plate's 17 position even after the indicator wire 6 is deployed from the tube 7.

Turning to FIG. 4B, the indicator wire 6 is fixedly attached to the lockout plate 17, which is coupled to a block 9 via the indicator spring 19. The block 9 is in a secured position, fixed to the housing 1 and/or the tube 7. Because the indicator wire 6 is connected to the tube 7 and/or housing 1 via a spring 19 and slidable lockout plate 17, the indicator wire 6 is capable of axial movement independent of the housing 1 and/or tube 7.

During operation, after the indicator wire 6 has been deployed through the puncture wound 400 with the formed loop 5 exposed to the lumen 420 of a vessel defined by a vessel wall 430, the operator is then ready to withdraw the device 100 and sheath 300 to deploy the sealing element 160 within the tract 410 of the puncture wound 400. Even if blood stops flowing out of the outlet port 23, that only indicates that the inlet port 22 is within the tract 410, not necessarily that the sealing element 160 is desirably near the edge 415 of the tract 410. However, the indicator wire 6 may provide such an indication. When the loop 5 of the wire 6 approaches the edge 415 of the tract 410, the loop 5 will engage the vessel wall 430 near the edge 415 as the device 100 is withdrawn by the operator. When the loop 5 engages the vessel wall 430, it will cause a force to be applied on the wire 6 toward the distal direction, or direction opposite that of the device 100 as its being withdrawn. This force will overcome the force of the spring 19 securing the lockout plate 17, proximally withdraw the lockout plate 17 in the distal direction, and cause the lockout plate 17 to disengage from the groove 18 of the rotary link 14, thereby unlocking the trigger 8. When the trigger 8 is unlocked, because the loop 5 has caught the edge 415, the distal end of the tube 7 is substantially adjacent to the edge 415 of the tract 410, which is a desirable location for the deployment of the sealing element 160. The operator is then enabled to deploy the sealing element 160.

Even though a spring loaded system is described above for locking and unlocking the trigger 8, one of ordinary skill in the art would appreciate that any locking mechanism may be employed in accordance with an embodiment of the present invention, such as a hydraulic and/or electronic system.

In addition to locking and unlocking the trigger 8, the indicator assembly 200 may also provide a visual and/or audio notification to the operator that the distal end of the tube 7 is in a desirable position. As will be explained in more detail with regard to FIGS. 4A, 4B, 5A, 5B, and 6, indicator 20 can be seen through indicator panel 13, which defines two windows 21, on the top plate 150 and indicates to the user when the appropriate time to depress trigger 8 with rotary link 14 has been reached.

Figure 5A:
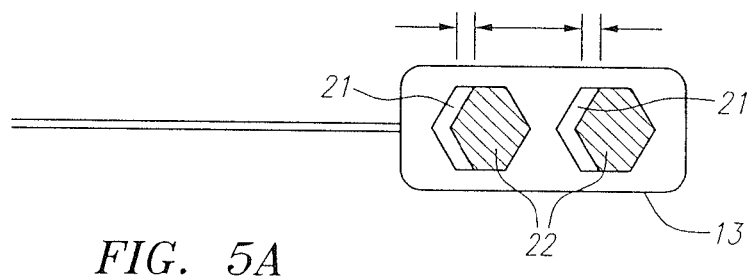
FIGS. 5(a-b) illustrate a top view of a window portion of the sealing element deployment device in accordance with a preferred embodiment of the present invention.
Figure 5B:
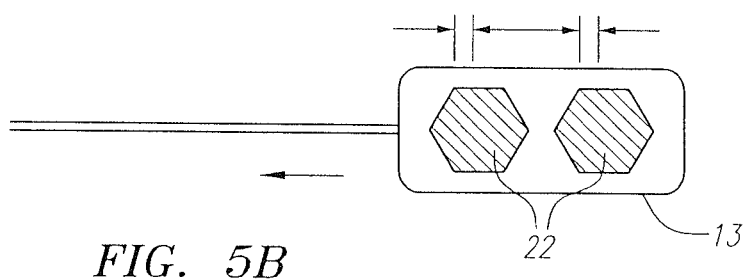

FIGS. 5A and 5B show a top view looking down through the windows 21, indicator 20 is provided with opaque portions 22. The windows 21 preferably have a shape consistent with the shape of markings 22 on the indicator 20. Thus, prior to the indicator wire 6 being axially displaced opposite of the housing 1 and/or tube 7, some or all of the windows 21 are clear, but when the indicator wire 6 is axially displaced opposite of the housing 1 and/or tube 7 as described above, markings 22 on the indicator 20 come into correspondence with the windows 21 of the indicator panel 13 as shown in FIG. 5B. When this registration occurs, trigger 8 may be depressed.

Figure 6:
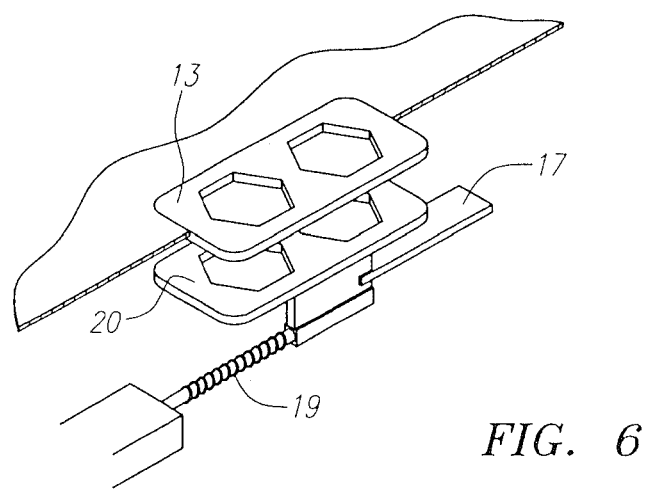
FIG. 6 illustrates a perspective view of a window portion of the sealing element deployment device in accordance with a preferred embodiment of the present invention.

FIG. 6 essentially shows the same thing as FIGS. 5A and 5B, but from a perspective view.

One of ordinary skill in the art would appreciate that though windows 21 are described, the indicator panel 21 may also utilize other mechanisms, such as electronic circuitry, light emitted diodes (LED), and/or other visual and/or audio mechanisms known in the art. For example, the device 100 may be configured such that when the indicator wire 6 engages the vessel wall 430 near the edge 415 of the tract 410, a circuit (not shown) is triggered within the housing 1 that causes a light to be emitted and/or an audio alarm to be invoked.

In the foregoing specification, the invention has been described with reference to specific embodiments thereof. It will, however, be evident that various modifications and changes may be made thereto without departing from the broader spirit and scope of the invention. For example, the reader is to understand that the specific ordering and combination of process actions described herein is merely illustrative, and the invention can be performed using different or additional process actions, or a different combination or ordering of process actions. As a further example, each feature of one embodiment can be mixed and matched with other features shown in other embodiments. Additionally and obviously, features may be added or subtracted as desired. Accordingly, the invention is not to be restricted except in light of the attached claims and their equivalents.

What is claimed:

1. A device for sealing a puncture in the wall of the body lumen comprising:
   an elongate deployment member having a sealing element releasably disposed within a distal end thereof, said deployment member being coupled to a first actuator configured to retract said deployment member relative to said sealing element,
   a pusher received by the deployment member, wherein the pusher supports the sealing element at a particular location within the deployment member, and
   an elongated indicator member having a proximal end and a distal end, said indicator member is a guide wire extending through a lumen in said deployment member such that the distal end of said indicator member is configured to form a loop when extended out distally of the distal end of the deployment member, and said indicator member being coupled to a second actuator configured to extend and retract said indicator member relative to said deployment member, wherein said second actuator is configured to extend said indicator member independent of said first and wherein operation of said first actuator retracts both said indicator member and said deployment member relative to said sealing element and said pusher.

2. The device of claim 1, wherein the first and second actuators are first and second gears, further wherein the first and second gears form first and second rack and pinion mechanisms respectively.

3. The device of claim 2, wherein the diameter of the first gear is substantially smaller than the diameter of the second gear.

4. The device of claim 2, wherein the rack and pinion mechanisms each have a mechanical advantage and the ratio of mechanical advantages for the first rack and pinion mechanism to the second rack and pinion mechanism is 2 to 1.

5. The device of claim 2, wherein the rack and pinion mechanisms each have a mechanical advantage and the ratio of mechanical advantages for the first rack and pinion mechanism to the second rack and pinion mechanism is 3 to 1.

6. The device of claim 1, wherein the first and second actuators are hydraulic devices.

7. The device of claim 1, wherein said device comprises a bleed back conduit defined in the deployment member.

8. The device of claim 1, wherein the first and second actuators are configured to withdraw the deployment member and indicator member respectively at different rates, wherein the rate of withdrawal for the indicator member is greater than the rate of withdrawal for the deployment member.

9. The device of claim 1, further comprising an inlet port coupled toward the distal end of the deployment member, configured to take in blood when exposed to a vessel, and an outlet port communicatively coupled to the inlet port configured to allow the blood that entered the inlet port to exit.

10. The device of claim 1, wherein the sealing element is expandable.

11. The device of claim 1, wherein the sealing element is comprised of bioabsorbable material.

12. The device of claim 1, wherein the device is configured to be engaged with an introducer sheath.

* * * * *